US008731674B2

(12) United States Patent
Wallace et al.

(10) Patent No.: US 8,731,674 B2
(45) Date of Patent: May 20, 2014

(54) METHOD OF STIMULATING FASTIGIUM NUCLEUS TO TREAT NEUROLOGICAL DISORDERS

(75) Inventors: Michael P. Wallace, Pleasanton, CA (US); James C. Makous, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/347,434

(22) Filed: Jan. 10, 2012

(65) Prior Publication Data

US 2012/0109234 A1  May 3, 2012

Related U.S. Application Data

(63) Continuation of application No. 11/761,330, filed on Jun. 11, 2007, now Pat. No. 8,103,350, and a continuation-in-part of application No. 10/893,076, filed on Jul. 16, 2004, now Pat. No. 7,286,879.

(51) Int. Cl.
*A61N 1/05* (2006.01)

(52) U.S. Cl.
USPC .................................. 607/45; 607/2; 607/116

(58) Field of Classification Search
USPC ............. 128/898, 899; 600/378; 607/2, 3, 45, 607/116–118
See application file for complete search history.

(56) References Cited

U.S. PATENT DOCUMENTS

| 4,141,365 A | 2/1979 | Fischell et al. |
| 4,285,347 A | 8/1981 | Hess |
| 4,519,403 A | 5/1985 | Dickhudt |
| 4,608,985 A | 9/1986 | Crish et al. |
| 4,658,835 A | 4/1987 | Pohndorf |
| 4,739,768 A | 4/1988 | Engelson |
| 4,813,934 A | 3/1989 | Engelson et al. |
| 4,869,255 A | 9/1989 | Putz |
| 4,884,579 A | 12/1989 | Engelson |
| 5,005,587 A | 4/1991 | Scott |
| 5,010,894 A | 4/1991 | Edhag |

(Continued)

FOREIGN PATENT DOCUMENTS

| EP | 0 861 676 | 9/1998 |
| EP | 0 865 800 A2 | 9/1998 |

(Continued)

OTHER PUBLICATIONS

Effects of electrical stimulation of medial olicocochlear neurons on ipsilateral and contralateral cochlear responses; Gifford, Margaret and Guinan, John Jr.; Hearing Research; Issue 29; 1987; pp. 179-194.*

(Continued)

*Primary Examiner* — Christopher D Koharski
*Assistant Examiner* — Pamela M Bays
(74) *Attorney, Agent, or Firm* — Vista IP Law Group LLP (57) ABSTRACT

A method of treating a neurological disorder comprises introducing an electrical stimulation lead within a patient's head, locating the stimulation lead within the $4^{th}$ ventricle of the patient's head, and placing the stimulation lead adjacent the fastigium nucleus of the patient's brain. The method may further comprise stimulating the fastigium nucleus with the stimulation lead to treat the neurological disorder, for example, by increasing the flow of blood within the patient's brain.

17 Claims, 6 Drawing Sheets

(56) References Cited

U.S. PATENT DOCUMENTS

| | | | |
|---|---|---|---|
| 5,170,802 A | 12/1992 | Mehra | |
| 5,224,491 A | 7/1993 | Mehra | |
| 5,234,437 A | 8/1993 | Sepetka | |
| 5,239,999 A | 8/1993 | Imran | |
| 5,250,071 A | 10/1993 | Palermo | |
| 5,261,916 A | 11/1993 | Engelson | |
| 5,263,488 A | 11/1993 | Van Veen et al. | |
| 5,304,195 A | 4/1994 | Twyford et al. | |
| 5,312,415 A | 5/1994 | Palermo | |
| 5,350,397 A | 9/1994 | Palermo et al. | |
| 5,365,926 A | 11/1994 | Desai | |
| 5,391,200 A | 2/1995 | KenKnight et al. | |
| 5,397,341 A | 3/1995 | Hirschberg et al. | |
| 5,411,551 A | 5/1995 | Winston et al. | |
| 5,417,719 A | 5/1995 | Hull et al. | |
| 5,423,864 A | 6/1995 | Ljungstroem | |
| 5,501,703 A | 3/1996 | Holsheimer et al. | |
| 5,509,411 A | 4/1996 | Littmann et al. | |
| 5,531,779 A | 7/1996 | Dahl et al. | |
| 5,534,007 A | 7/1996 | St. Germain et al. | |
| 5,543,864 A | 8/1996 | Hirschman et al. | |
| 5,603,731 A | 2/1997 | Whitney | |
| 5,647,870 A | 7/1997 | Kordis et al. | |
| 5,683,422 A | 11/1997 | Rise | |
| 5,702,438 A | 12/1997 | Avitall | |
| 5,707,354 A | 1/1998 | Salmon et al. | |
| 5,713,922 A | 2/1998 | King | |
| 5,716,377 A | 2/1998 | Rise et al. | |
| 5,752,979 A | 5/1998 | Benabid | |
| 5,782,239 A | 7/1998 | Webster, Jr. | |
| 5,792,187 A | 8/1998 | Adams | |
| 5,800,474 A | 9/1998 | Benabid et al. | |
| 5,814,062 A | 9/1998 | Sepetka et al. | |
| 5,833,709 A | 11/1998 | Rise et al. | |
| 5,846,238 A | 12/1998 | Jackson et al. | |
| 5,860,974 A | 1/1999 | Abele | |
| 5,871,483 A | 2/1999 | Jackson et al. | |
| 5,891,136 A | 4/1999 | McGee et al. | |
| 5,902,236 A | 5/1999 | Iversen | |
| 5,908,385 A | 6/1999 | Chechelski et al. | |
| 5,925,070 A | 7/1999 | King et al. | |
| 5,938,689 A | 8/1999 | Fischell et al. | |
| 5,954,761 A | 9/1999 | Machek et al. | |
| 5,967,986 A | 10/1999 | Cimochowski et al. | |
| 6,006,134 A | 12/1999 | Hill et al. | |
| 6,015,387 A | 1/2000 | Schwartz et al. | |
| 6,016,449 A | 1/2000 | Fischell et al. | |
| 6,018,682 A | 1/2000 | Rise | |
| 6,024,702 A * | 2/2000 | Iversen | 600/378 |
| 6,027,456 A | 2/2000 | Feler et al. | |
| 6,053,873 A | 4/2000 | Govari et al. | |
| 6,066,163 A | 5/2000 | John | |
| 6,074,407 A | 6/2000 | Levine et al. | |
| 6,074,507 A | 6/2000 | Sukenik | |
| 6,091,980 A | 7/2000 | Squire et al. | |
| 6,094,596 A | 7/2000 | Morgan | |
| 6,119,044 A | 9/2000 | Kuzma | |
| 6,122,548 A | 9/2000 | Starkebaum et al. | |
| 6,128,538 A | 10/2000 | Fischell et al. | |
| 6,136,021 A | 10/2000 | Tockman et al. | |
| 6,141,576 A | 10/2000 | Littmann et al. | |
| 6,161,029 A | 12/2000 | Spreigl et al. | |
| 6,161,047 A | 12/2000 | King et al. | |
| 6,167,311 A | 12/2000 | Rezai | |
| 6,170,488 B1 | 1/2001 | Spillman, Jr. et al. | |
| 6,179,858 B1 | 1/2001 | Squire et al. | |
| 6,205,361 B1 | 3/2001 | Kuzma et al. | |
| 6,216,045 B1 | 4/2001 | Black et al. | |
| 6,231,516 B1 | 5/2001 | Keilman et al. | |
| 6,249,707 B1 | 6/2001 | Kohnen et al. | |
| 6,263,248 B1 | 7/2001 | Farley et al. | |
| 6,266,568 B1 | 7/2001 | Mann et al. | |
| 6,319,251 B1 | 11/2001 | Tu et al. | |
| 6,330,477 B1 | 12/2001 | Casavant | |
| 6,353,762 B1 | 3/2002 | Baudino et al. | |
| 6,360,122 B1 | 3/2002 | Fischell et al. | |
| 6,361,528 B1 | 3/2002 | Wilson et al. | |
| 6,370,427 B1 | 4/2002 | Alt et al. | |
| 6,391,052 B2 | 5/2002 | Buirge et al. | |
| 6,393,325 B1 | 5/2002 | Mann et al. | |
| 6,397,109 B1 | 5/2002 | Cammilli et al. | |
| 6,402,746 B1 | 6/2002 | Whayne et al. | |
| 6,408,214 B1 | 6/2002 | Williams et al. | |
| 6,415,187 B1 | 7/2002 | Kuzma et al. | |
| 6,418,344 B1 | 7/2002 | Rezai et al. | |
| 6,438,427 B1 | 8/2002 | Rexhausen et al. | |
| 6,442,413 B1 | 8/2002 | Silver | |
| 6,442,435 B2 | 8/2002 | King et al. | |
| 6,445,953 B1 | 9/2002 | Bulkes et al. | |
| 6,463,328 B1 | 10/2002 | John | |
| 6,466,822 B1 | 10/2002 | Pless | |
| 6,480,743 B1 | 11/2002 | Kirkpatrick et al. | |
| 6,484,059 B2 | 11/2002 | Gielen | |
| 6,516,227 B1 | 2/2003 | Meadows et al. | |
| 6,519,488 B2 | 2/2003 | KenKnight et al. | |
| 6,522,932 B1 | 2/2003 | Kuzma et al. | |
| 6,529,774 B1 | 3/2003 | Greene | |
| 6,539,263 B1 | 3/2003 | Schiff et al. | |
| 6,547,788 B1 | 4/2003 | Maguire et al. | |
| 6,547,870 B1 | 4/2003 | Griessmann et al. | |
| 6,562,063 B1 | 5/2003 | Euteneuer et al. | |
| 6,584,358 B2 | 6/2003 | Carter et al. | |
| 6,587,733 B1 | 7/2003 | Cross, Jr. et al. | |
| 6,589,230 B2 | 7/2003 | Gia et al. | |
| 6,591,138 B1 | 7/2003 | Fischell et al. | |
| 6,597,953 B2 | 7/2003 | Boling | |
| 6,600,954 B2 | 7/2003 | Cohen et al. | |
| 6,606,521 B2 | 8/2003 | Paspa et al. | |
| 6,647,296 B2 | 11/2003 | Fischell et al. | |
| 6,658,302 B1 | 12/2003 | Kuzma et al. | |
| 6,662,055 B1 | 12/2003 | Prutchi | |
| 6,665,562 B2 | 12/2003 | Gluckman et al. | |
| 6,690,974 B2 | 2/2004 | Archer et al. | |
| 6,697,676 B2 | 2/2004 | Dahl et al. | |
| 6,842,648 B2 | 1/2005 | Partridge et al. | |
| 6,895,283 B2 | 5/2005 | Erickson et al. | |
| 6,978,180 B2 | 12/2005 | Tadlock | |
| 7,052,486 B2 | 5/2006 | Hildebrand | |
| 7,286,879 B2 | 10/2007 | Wallace | |
| 7,295,875 B2 | 11/2007 | Wallace et al. | |
| 7,340,298 B1 * | 3/2008 | Barbut | 607/2 |
| 2001/0025192 A1 | 9/2001 | Gerber et al. | |
| 2001/0041821 A1 | 11/2001 | Wilk | |
| 2001/0053885 A1 | 12/2001 | Gielen et al. | |
| 2002/0087201 A1 | 7/2002 | Firlik et al. | |
| 2002/0111661 A1 | 8/2002 | Cross, Jr. et al. | |
| 2002/0151948 A1 | 10/2002 | King et al. | |
| 2002/0151949 A1 | 10/2002 | Dahl et al. | |
| 2002/0188207 A1 | 12/2002 | Richter | |
| 2003/0014016 A1 | 1/2003 | Purdy | |
| 2003/0040785 A1 | 2/2003 | Maschino et al. | |
| 2003/0149450 A1 * | 8/2003 | Mayberg | 607/3 |
| 2003/0199962 A1 | 10/2003 | Struble et al. | |
| 2003/0204135 A1 | 10/2003 | Bystritsky | |
| 2003/0204228 A1 | 10/2003 | Cross et al. | |
| 2004/0015193 A1 | 1/2004 | Lamson et al. | |
| 2004/0133184 A1 * | 7/2004 | Hildebrand | 604/508 |
| 2005/0137646 A1 | 6/2005 | Wallace et al. | |
| 2005/0187589 A1 | 8/2005 | Wallace et al. | |
| 2006/0015152 A1 | 1/2006 | Wallace | |

FOREIGN PATENT DOCUMENTS

| | | |
|---|---|---|
| EP | 0 865 800 A3 | 12/1999 |
| EP | 0 865 800 B1 | 9/2004 |
| WO | WO 01/85094 | 11/2001 |
| WO | WO 03/077986 | 9/2003 |

OTHER PUBLICATIONS

Web Article: IP.com: "Methods of Placement of Neurostimulation Lead, Infusion Catheter, and/or Sensor Via Peripheral Vasculature." IPCOM000012136D; Apr. 10, 2003; 8 Pages.*

Evaluation of Surgical Approaches to of Endoscopic Auditory (56) References Cited

OTHER PUBLICATIONS

Brainstem Implantation; Friedland, David and Wackym, Phillip; The Laryngoscope, Issue 109; 1999; pp. 175-180.

Canavero, Sergio et al., "Extradural Motor Cortex Stimulation for Advanced Parkinson Disease," J. Neurosurg. 97: pp. 1208-1211, 2002.

Kunieda, Takeharu et al., "Use of Cavernous Sinus EEG in the Detection of Seizure Onset and Spread in Mesial Temporal Lobe Epilepsy," Epilepsia, 41(11): pp. 1411-1419, 2000.

Onal, Cagatay, et al. "Complications of Invasive Subdural Grid Monitoring in Children with Epilepsy," J. Neurosurg. 98: pp. 1017-1026, 2003.

PCT International Search Report for PCT/US2005/006569, Applicant: Boston Scientific Scimed, Inc., Forms PCT/ISA 210 and 220, dated Jun. 13, 2005 (7 pages).

PCT Written Opinion of the International Search Authority for PCT/US2005/006569, Applicant: Boston Scientific Scimed, Inc., Form PCT/ISA/237, dated Jun. 13, 2005 (5 pages).

PCT International Search Report for PCT/US2005/010121, Applicant: Boston Scientific Scimed, Inc., Forms PCT/ISA/210 and 220, dated Jul. 4, 2005 (7 pages).

PCT Written Opinion of the International Search Authority for PCT/US2005/010121, Applicant: Boston Scientific Scimed, Inc., Form PCT/ISA/237, dated Jul. 4, 2005 (5 pages).

Web Article: IP.com: "Dual Lumen Inflatable Lead." File://c:\unzipped\IPCOM000019703D1\0_properties.xml, Published Sep. 25, 2003 (7 pages).

Web Article: IP.com: "Electrode Design to Stimulate Blood Vessels, Nerves, or Other Tubular Organs." File://c:\unzipped\IPCOM000010247D1\0_properties.xml, Published Nov. 13, 2002 (13 pages).

Web Article: IP.com: "Epidural Needle for Spinal Cord Stimulation Electrode." File://c:\unzipped\IPCOM000011384D1\0_properties.xml, Published Feb. 14, 2003 (6 pages).

Web Article: IP.com: "Medical Lead System and Method for Insertion into the Spinal Cord." File://c:\unzipped\IPCOM000011389D1\0_properties.xml, Published Feb. 17, 2003 (7 pages).

Web Article: IP.com: "Methods and Placement of Neurostimulation Lead, Infusion Catheter, and/or Sensor Via the Vasculature to the Brain." IPCOM000012135D, Published Apr. 10, 2003 (11 pages).

Web Article: IP.com: "Methods of Placement of Neurostimulation Lead, Infusion Catheter, and/or Sensor Via Peripheral Vasculature." 0349945-003 (7 pages), 2003.

Web Article: IP.com: "Skull-Mounted Electrical Stimulation System." File://c:\unzipped\IPCOM000019827D1\0_properties.xml, Published Oct. 1, 2003 (29 pages).

Web Article: IP.com: "Skull-Mounted Electrical Stimulation System and Method for Treating Patients." File://c:\unzipped\IPCOM000021554D1\0_properties.xml, Published Jan. 22, 2004 (31 pages).

Web Article: IP.com: "Spinal Cord Stimulation as a Therapy for Epilepsy." File://c:\unzipped\IPCOM000019881D1\0_properties.xml, Published Oct. 6, 2003 (10 pages).

Web Article: IP.com: "System and Method for Lead Fixation." File://c:\unzipped\IPCOM000019571D1\0_properties.xml, Published Sep. 19, 2003 (11 pages).

Web Article: IP.com: "Transcutaneous Screening Test for Evaluation of Potential Efficacy of Chronic Trigeminal Neurostimulation as a Therapy for Epilepsy." File://c:\unzipped\IPCOM000011987D1\0_properties.xml, Published Mar. 28, 2003 (8 pages).

Reis, D.J., et al., "Electrical Stimulation of Cerebellar Fastigial Nucleus Reduces Ischemic Infarction Elicited by Middle Cerebral Artery Occlusion in Rat," Journal of Cerebral Blood Flow and Metabolism, 11:(5):810-818 (Sep. 1991).

Golanov, E.V., et al., "Stimulation of Cerebellum Protects Hippocampal Neurons from Global Ischemia," Neuroreport, 9(5):819-824 (Mar. 30, 1998).

Galea, E., et al., "Cerebellar Stimulation Reduces Inducible Nitric Oxide Synthase Expression and Protects Brain from Ischemia," Am J Physiol Heart Circ Physiol, 274:H2035-H2045 (Jun. 1998).

Galea, E., et al., "Stimulation of Cerebellar Fastigial Nucleus Inhibits Interleukin-1β-induced Cerebrovascular Inflammation," Am J Physiol, 275:H2053-H2063 (Dec. 1998).

Golanov, E.V., et al., "Neuroprotective Electrical Stimulation of Cerebellar Fastigial Nucleus Attenuates Expression of Periinfaction Depolarizing Waves (PIDs) and Inhibits Cortical Spreading Depression," Brain Res, 818:304-315 (Feb. 1999).

\* cited by examiner

METHOD OF STIMULATING FASTIGIUM NUCLEUS TO TREAT NEUROLOGICAL DISORDERS

RELATED APPLICATIONS

This application is a continuation application of copending U.S. patent application Ser. No. 11/761,330, filed Jun. 11, 2007, which is a continuation-in-part application of U.S. patent application Ser. No. 10/893,076, filed Jul. 16, 2004 (now U.S. Patent No. 7,286,879), which is expressly incorporated herein by reference.

FIELD OF THE INVENTION

The invention relates to the treatment of neurological disorders, and in particular, the treatment of neurological disorders, such as acute stroke, using electrical leads.

BACKGROUND OF THE INVENTION

Several animal studies have disclosed that the electrical stimulation of the fastigium nucleus (FN), which forms a portion of the cerebellum, can have dramatic effects on reducing the core infarction size and surrounding penumbra after the onset of an ischemic stroke. For example, one study suggests that the stimulation of the FN for just one hour provides ten days worth of neuroprotection. Another study suggests that the infarction volume can be reduced by at least forty percent when the FN is stimulated after a stroke. The mechanism used to provide neuroprotection via FN stimulation is not well understood, but the studies have suggested that stimulation of the FN suppresses tissue damaging inflammation of brain tissue otherwise brought on by the overproduction of enzymes in response to the ischemic event. In all of the animal studies, the FN was electrically stimulated via a highly invasive surgical procedure.

Currently, the stimulation treatment of various neurological disorders in humans, including ischemic stroke, as well as Alzheimer's Disease, Parkinson's Disease, Tremor, and Epilepsy, can be accomplished via a substantially invasive procedure, which involves first drilling a burr hole through the patient's cranium in order to gain access to the brain tissue. A stimulation lead, and in particular, a lead with multiple electrodes extending along its length, is then introduced through one or more burr holes into contact with the selected brain tissue. In a deep brain stimulation (DBS) procedure, typically used to treat Parkinson's Disease, Tremor, and Epilepsy, the stimulation lead is advanced through a burr hole deep into the brain, e.g., the anterior thalamus, ventrolateral thalamus (Thal), internal segment of globus pallidus (GPi), substantia nigra pars reticulata (SNr), subthalamic nucleus (STN), external segment of globus pallidus (GPe), and neostriatum. In a cortical brain stimulation procedure, typically used to rehabilitate stroke victims, the lead is introduced through two burr holes and placed underneath the dura matter in contact with the cortex of the brain.

Once the lead is properly located in contact with the selected brain tissue, an electrical stimulator can be connected to the lead and operated to convey therapeutic electrical energy to the selected brain tissue. Depending on the period of treatment, the electrical stimulator may be implanted, in which case, the proximal end of the lead or an extension lead can be subcutaneously routed from the burr hole underneath the patient's scalp, down the neck, and into the chest or abdominal region in electrical connection with an implanted electrical stimulator.

Although the current brain stimulation techniques used to treat neurological disorders have proven to be successful, none of the previous techniques suggest a less invasive approach for stimulating the FN to treat ischemic stroke. That is, such techniques are still quite invasive, requiring the cranium to be opened through at least one burr hole, and entirely delivered through brain tissue to reach the stimulation site.

Thus, there remains a need to provide an improved method of electrically stimulating the FN to treat neurological disorders, such as ischemic stroke.

SUMMARY OF THE INVENTION

In accordance with one aspect of the present inventions, a method of treating a disorder in a patient is provided. The method particularly lends itself well to the treatment of neurological disorders—especially those disorders that can be alleviate by increasing the flow of blood within the patient's brain, such as acute stroke, chronic transient ischemic attack, cerebral vasospasm, and Alzheimer's Disease.

The method comprises introducing an electrical stimulation lead within the patient's head. The stimulation lead can, e.g., be intravascularly introduced into the head via the circulatory system or ventricular system, or introduced into the head through a cranial burr hole. The method further comprises advancing the stimulation lead within an intracranial vascular body. As examples, the vascular body can be an artery, such as a posterior inferior cerebellar artery, a vein, such as the preculminate vein, or a ventricular body, such as the $4^{th}$ ventricle.

The method further comprises placing the stimulation lead adjacent a selected structure of the patient's brain, such as a hindbrain structure of the brain, e.g., the fastigium nucleus. The stimulation lead may either be placed in direct contact or indirect contact with the fastigium nucleus as long as the stimulation energy can be conveyed from the stimulation lead to the selected brain structure to provide the desired therapeutic effect. In one method, the stimulation lead is connected to a stimulation source, and electrical energy is conveyed from the stimulation source to the stimulation lead to treat the disorder. Preferably, the stimulation increases the flow of blood in the patient's brain to treat the disorder. In an optional method, the method further comprises introducing another electrical stimulation lead within the head of the patient, and placing the other stimulation lead adjacent cortical tissue of the patient's brain, the stimulation of which treats the patient. For example, if the neurological disorder an acute stroke, stimulation of the cortical tissue may help rehabilitate the patient.

In accordance with another aspect of the present inventions, another method of treating a neurological disorder in a patient is provided. As with the previous method, this method particularly lends itself well to the treatment of neurological disorders—especially those disorders that can be alleviate by increasing the flow of blood within the patient's brain, such as acute stroke, chronic transient ischemic attack, cerebral vasospasm, and Alzheimer's Disease. The method comprises introducing an electrical stimulation lead within the patient's head, locating the stimulation lead within the $4^{th}$ ventricle of the patient's head, and placing the stimulation lead adjacent the fastigium nucleus of the patient's brain.

In one method, the stimulation lead is introduced into the patient's head via the ventricular system. For example, the stimulation lead can be introduced into the patient's head by advancing the stimulation lead along the intrathecal space along the spinal column of the patient. In this case, the stimulation lead may be located within the $4^{th}$ ventricle by advancing the stimulation lead from the intrathecal space into the 4$^{th}$ ventricle via the foramen of Magendie or one of the foramina of Luschka. In another method, the stimulation lead is introduced into the patient's head via a burr hole. In this case, the stimulation lead may be located within the 4$^{th}$ ventricle by introducing the stimulation lead into the 3$^{rd}$ ventricle of the patient's head and advancing the stimulation lead from the 3$^{rd}$ ventricle into the 4$^{th}$ ventricle via the Sylvian aqueduct. The stimulation lead may be introduced into the 3$^{rd}$ ventricle by advancing the stimulation lead from the burr hole through the frontal lobe of the patient's brain into the lateral ventricle of the patient's head, and from the lateral ventricle into the 3$^{rd}$ ventricle via the foramen of Monroe.

One method comprises stimulating the fastigium nucleus with the stimulation lead to treat the neurological disorder, e.g., to increase the flow of blood within the patient's brain. Another method comprises introducing another electrical stimulation lead within the head of the patient, placing the other stimulation lead adjacent cortical tissue of the patient's brain, and stimulating the cortical tissue with the other stimulation lead to rehabilitate the patient.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DETAILED DESCRIPTION OF THE PREFERRED EMBODIMENTS

Figure 1:
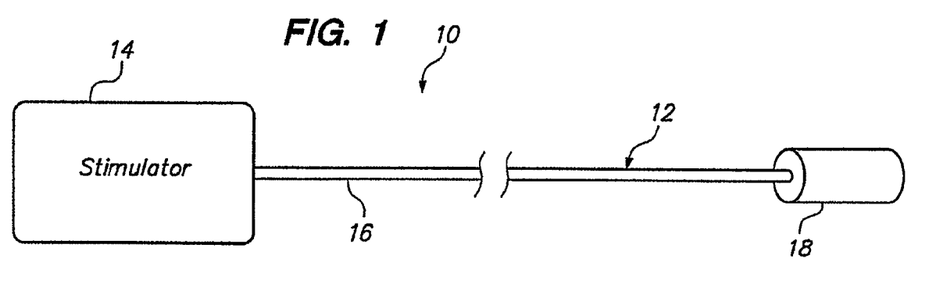
FIG. 1 is a plan view of an intravascular brain stimulation system constructed in accordance with a preferred embodiment of the present invention.

Referring now to FIG. 1, an intravascular brain stimulation system 10 constructed in accordance with one preferred embodiment of the present invention is shown. In its simplest form, the stimulation system 10 generally comprises a first stimulation lead 12 configured to be introduced adjacent a selected structure of a patient's brain, and an implantable electrical stimulation source 14 configured for delivering stimulation energy to the stimulation lead 12. In alternative embodiments, multiple stimulation leads 12 can be provided.

The stimulation lead 12 comprises a flexible electrically conductive signal wire 16 and a single electrode 18 mounted at the distal end of the wire 16 using suitable connection means, such as soldering or welding. In the illustrated embodiment, the electrode 18 is cylindrically shaped and has a size that allows it to be delivered through a delivery catheter. The wire 16 comprises an electrically conductive core with an outer insulative layer. The length of the wire 16 is preferably sized to extend from the selected stimulation site in the brain (which in this case, is the fastigium nucleus located in the cerebellum of the brain) to the remotely located stimulation source 14, which will typically be located outside of the patient's body, but may optionally be implanted. The electrode 18 is composed of a biocompatible and electrically conducting material, such as copper alloy, platinum, stainless steel, or nitinol. The electrically conducting material of the electrode 18 can be further coated with platinum-iridium or gold to improve its conduction properties, biocompatibility, and radiopacity. To prevent blood clotting, the electrode lead 12 can be optionally coated with a non-thrombogenic agent.

Figure 2:
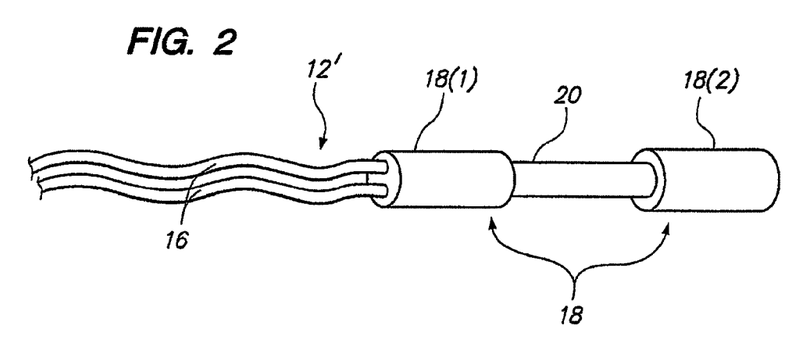
FIG. 2 is a perspective view of an alternative embodiment of an intravascular stimulation lead that can be used in the system of FIG. 1.

Referring to FIG. 2, an alternative embodiment of a stimulation electrode lead 12' is shown. The stimulation lead 12' is similar to the previously described stimulation lead 12, with the exception that it comprises a pair of electrodes 18 (a proximal electrode 18(1) and a distal electrode 18(2)) and a pair of signal wires 16 respectively coupled to the pair of electrodes 18. The electrode pair 18 can be suitably formed, e.g., by mounting a pair of ring electrodes around an electrically insulative cylindrical core 20, or by coating the cylindrical core 20 with electrically conductive material. The signal wires 16 extend through the cylindrical core 20 into contact with the respective electrodes 18(1) and 18(2). Thus, it can be appreciated that the stimulation lead 12', by itself, can be operated in a bipolar mode. This is in contrast to the stimulation lead 12, which can be operated in a monopolar mode, or alternatively, can be operated in a bipolar mode in conjunction with another stimulation lead 12, as will be described in further detail below.

It should be noted that the intravascular stimulation leads 12 or 12' may have different structures than that illustrated in FIGS. 1 and 2. For example, the intravascular stimulation leads 12 or 12' may alternatively or optionally have a stent electrode, arrayed electrode structure, basket electrode structure, inflatable electrode structure, helical electrode structure, etc., may take the form of a guidewire or catheter, and may have optional blood occlusion features, such as a balloon or RF ablation electrode, the details of which are disclosed in U.S. patent application Ser. No. 10/744,319, entitled "Method of Intravascularly Delivering Stimulation Leads into the Brain", which is expressly incorporated herein by reference.

Referring back to FIG. 1, the implantable stimulation source 14 is designed to deliver electrical pulses to the stimulation lead 12 in accordance with programmed parameters. In the preferred embodiment, the stimulation source 14 is programmed to output electrical pulses having amplitudes varying from 0.1 to 20 volts, pulse widths varying from 0.02 to 1.5 milliseconds, and repetition rates varying from 2 to 2500 Hertz. In the illustrated embodiment, the stimulation source 14 takes the form of a totally self-contained generator. The stimulation source 14 may optionally be configured to be implanted within the patient's body. The stimulation source 14 is connected to the stimulation lead 12 is a monopolar arrangement, or may be connected to multiple stimulation leads 12 or the stimulation lead 12' in a monopolar arrangement or a bipolar arrangement. Further details regarding stimulation sources and various techniques of connecting stimulation leads to stimulation sources are described in U.S. patent application Ser. No. 10/744,319, which has previously been incorporated herein by reference.

Having described the structure of the intravascular brain stimulation system 10, a preferred method of installing it within a patient's body in order to treat a diagnosed neurological disorder within the brain, and in particular an acute stroke, will now be described. In the preferred method, the stimulation lead will be placed adjacent the fastigium nucleus (FN), which can then be electrically stimulated to increase collateral blood flow within the brain, thereby reducing the size of, or perhaps eliminating altogether, the infarction otherwise resulting from the acute stroke.

In order to minimize the invasiveness of the procedure, at least a portion of the preexisting vasculature (e.g., the circulatory or ventricular system) of the patient is utilized to gain access to the FN. This can be accomplished, e.g., by first introducing the stimulation lead into the patient's head via the selected vascular system and then advancing the stimulation lead within selected cerebral vascular bodies within that system until the active portion of the stimulation lead is adjacent the FN, or alternatively, by first non-vascularly introducing the stimulation lead into the patient's head (e.g., through a burr hole in the cranium) and then advancing the stimulation lead within vascular bodies of a selected vascular system until the stimulation lead is adjacent the FN. The former case is less invasive than the latter case, since it entirely uses the vasculature to both introduce the stimulation lead into the patient's head and, once inside the head, deliver the stimulation lead to a site adjacent the FN. Additional stimulation leads can optionally be placed adjacent the FN as necessary.

A standard imaging system, such as Computed Tomography Angiography (CTA), fluoroscopy, Magnetic Resonance Imaging (MRI), and/or ultrasound, and a standard delivery mechanism, such as a guide wire, delivery catheter, and/or guide sheath (all not shown), can be used to facilitate delivery of the stimulation lead into the patient's head and/or route the stimulation lead to a location adjacent the FN. Of course, if the stimulation lead, itself takes the form of a guidewire or catheter, a separate guide wire or catheter may not be needed. The stimulation lead may be maintained within the vascular body adjacent the FN, such that stimulation can be indirectly applied to the FN, or alternatively, can be inserted through a puncture within the vascular body into direct contact with the FN with the aid of a stylet. If the stimulation lead has an anchoring capability (e.g., it has as a stent electrode, arrayed electrode structure, basket electrode structure, inflatable electrode structure, helical electrode structure, etc), the stimulation lead can be deployed in order to stabilize the stimulation lead relative to the FN. Further details describing the delivery and deployment of stimulation leads into indirect or direct contact with brain tissue are provided in U.S. patent application Ser. No. 10/744,319, which has previously been incorporated herein by reference.

Optionally, another stimulation lead (which may be either similar as or different from first stimulation lead) can be introduced adjacent other structures of the brain, and in this case, the cortical tissue of the brain. This stimulation lead may be intravascularly placed adjacent the cortical tissue, e.g., along the superior saggital sinus (not shown), or epidurally or subdurally placed along the cortical tissue via a burr hole previously formed within the patient's cranium. Notably, assuming that some damage to the brain has been caused by the stroke, electrical stimulation of the cortical tissue using the other stimulation lead may help rehabilitate the patient. Further details describing the delivery and deployment of stimulation leads into indirect or direct contact with cortical tissue are provided in U.S. patent application Ser. No. 10/783,679, entitled "Method of Stimulating/Sensing Brain with Combination of Intravascularly and Non-Vascularly Delivered Leads," which is expressly incorporated herein by reference.

After the stimulation lead(s) have been deployed within the brain, their proximal ends will remain outside of the patient's body after the stimulation deployment process is completed. For example, if a stimulation lead is intravascularly introduced into the patient's head via the circulatory system, the proximal end stimulation lead will extend from a venous or arterial access point. If the stimulation lead is intravascularly introduced into the patient's head via the ventricular system, the proximal end of the stimulation lead will extend from the intrathecal space of the patient's spine. If the stimulation lead is introduced into the patient's head via a burr hole, the proximal end of the cranial burr hole will extend from the burr hole.

The exposed proximal ends of the stimulation lead(s) can then be coupled to the stimulation source in either a monopolar arrangement or a bipolar arrangement. Typically, the stimulation lead used to stimulate the FN will be left in the brain acutely (i.e., only during an operation and then removed after the operation has been completed). In this case, the stimulation source will not be implanted, but instead will be located externally to the patient. The optional cortical stimulation lead, however, should be left in the brain chronically or sub-chronically (i.e., less than six months) in order to provide rehabilitation of the patient over an extended period of time. In this case, the stimulation source will be implanted within the patient's body (e.g., in the clavical or chest region or behind the ear of the patient), and the optional stimulation lead can be subcutaneously routed to this implantation site. The stimulation source may then be operated to provide electrical stimulation energy to the FN, thereby minimizing the size of the infarct created by the acute stroke, and optionally, provide electrical stimulation energy to the cortical tissue, thereby rehabilitating the patient. Stimulation of the FN and cortical tissue may be accomplished simultaneously, but typically, the FN will be stimulate to control the effects of the acute stroke, and the cortical tissue will then be subsequently stimulated to rehabilitate the patient.

Figure 3:
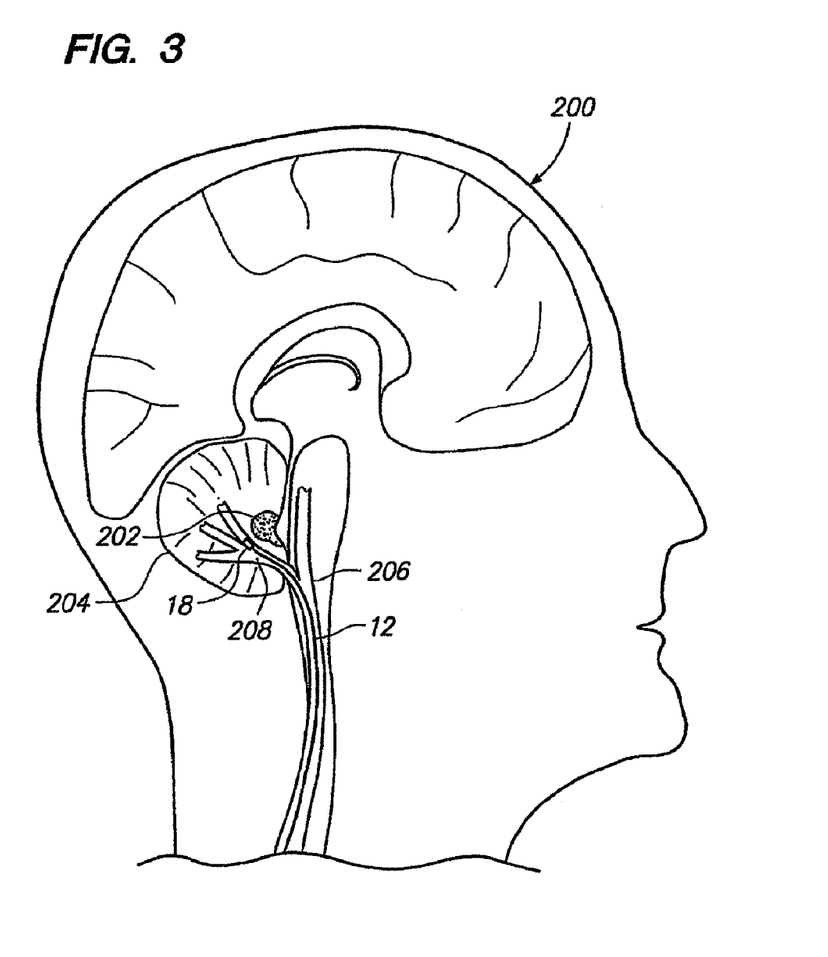
FIG. 3 is a lateral view of one hemisphere of a patient's brain, particularly illustrating a method of intravascular routing of the stimulation lead of the system of FIG. 1 via the arterial system.

As briefly discussed above, the stimulation lead can be placed adjacent the FN via an intravascular body in any one of a variety of manners. In one example shown in FIG. 3, the stimulation lead 12 is intravascularly delivered into the patient's head 200 via an artery, and in this case the vertebral artery 206, and then routed through select arteries within the cerebral arterial system until the electrode 18 of the lead 12 is adjacent the fastigium nucleus (FN) 202 of the cerebellum 204. The point at which the arterial system can be accessed can be any remote access point, including the vertebral artery 206, itself, or the femoral artery (not shown). As illustrated in FIG. 3, the specific arterial route taken by the stimulation lead 12 to obtain access to the FN 202 from the vertebral artery 206 terminates in the posterior inferior cerebellar artery (PICA) 208 or an artery branching from the PICA 208. Notably, the PICA 208 in a typical adult human is approximately three millimeters from the FN 202, which should be sufficiently close enough to provide indirect therapeutic stimulation to the FN 202 via the PICA 208. As previously discussed, however, the stimulation lead 12 can be inserted through a puncture within the PICA 208 into direct contact with the FN 202 with the aid of a stylet.

Figure 4:
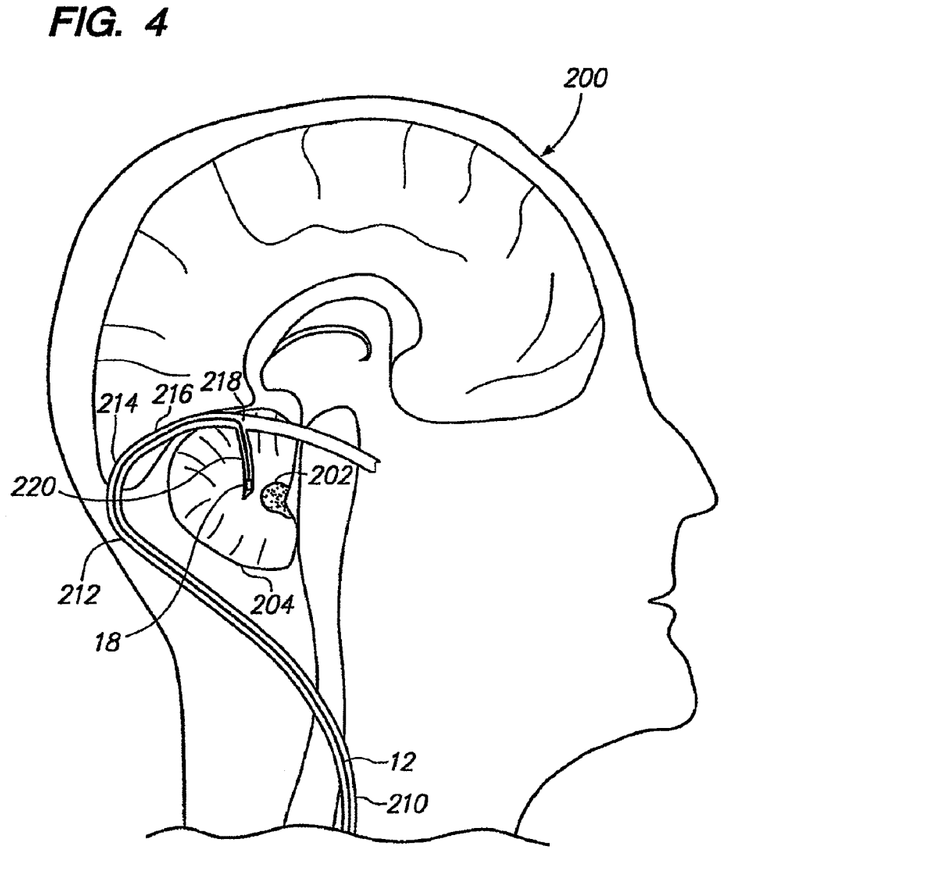
FIG. 4 is a lateral view of one hemisphere of a patient's brain, particularly illustrating a method of intravascular routing of the stimulation lead of the system of FIG. 1 to a site adjacent the fastigium nucleus via the venous system.

In another example shown in FIG. 4, the stimulation lead 12 may be intravascularly delivered into the patient's head 200 via a vein, and in this case the jugular vein 210, and then routed through select veins within the cerebral venous system until the electrode 18 of the lead 12 is adjacent the fastigium nucleus (FN) 202. The point at which the arterial system can be accessed can be any remote access point, including the jugular vein 210, itself, or the femoral vein (not shown). As illustrated in FIG. 4, the specific venous route taken by the stimulation lead 12 to obtain access to the FN 202 from the jugular vein 210 goes through the sigmoid sinus 212, the straight sinus 214, the vein of galen 216, and the superior cerebellar vein 218, and terminates in the preculminate vein 220. Notably, the preculminate vein 220 in a typical adult human is approximately 2-30 millimeters from the FN 202, which should be sufficiently close enough to provide indirect therapeutic stimulation to the FN 202. As previously discussed, however, the stimulation lead 12 can be inserted through a puncture within the preculminate vein 220 into direct contact with the FN 202 with the aid of a stylet.

Figure 5:
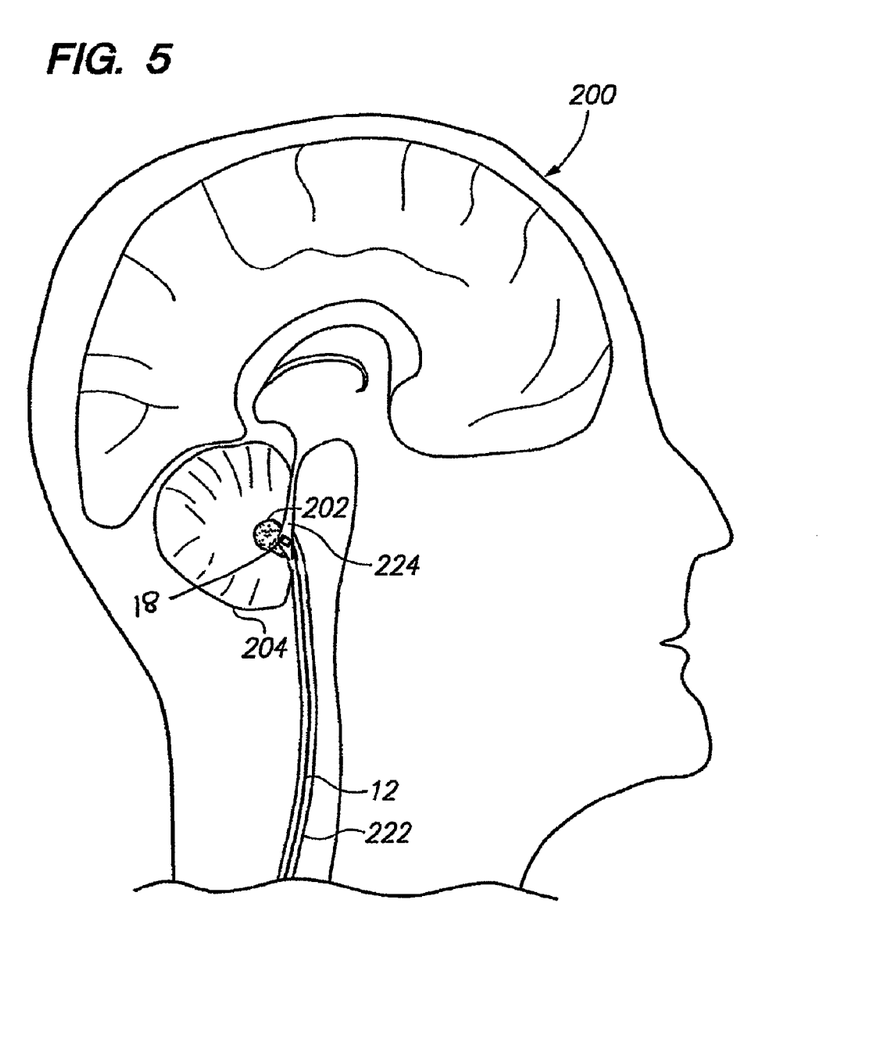
FIG. 5 is a lateral view of one hemisphere of a patient's brain, particularly illustrating a method of intravascular routing of the stimulation lead of the system of FIG. 1 to a site adjacent the fastigium nucleus via the ventricular system.
Figure 7:
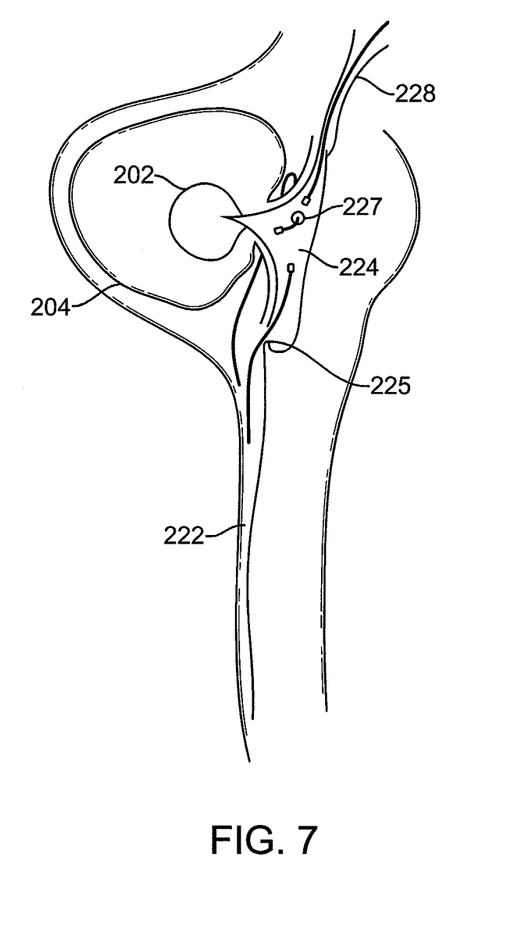
FIG. 7 is a lateral view of ventricular system of a patient, particularly showing the introduction of stimulation leads within the 4$^{th}$ ventricle via different entry points.

In still another example shown in FIG. 5, the stimulation lead 12 may be intravascularly delivered into the patient's head 200 via the ventricular system, and in this case the intrathecal space 222, and then routed through select ventricles of the brain until the electrode 18 of the lead 12 is adjacent the fastigium nucleus (FN) 202. This sentence appears to be missing words: The point at which the lead 12 is introduced into the intrathecal space 222 can be anywhere along the spinal column, but preferably, is in the lumbar region or up near the cervical region. As best illustrated in FIG. 7, the specific ventricular route taken by the stimulation lead 12 to obtain access to the FN 202 from the intrathecal space 222 goes through the foramen of Magendie 225 or one of the foramina of Luschka 227 (only one shown in FIG. 7) and into the 4$^{th}$ ventricle 224. Notably, the 4$^{th}$ ventricle 224 allows the stimulation lead 12 to be placed into direct contact with the FN 202 without piercing the cerebellum 204. If desired, the lead 12 may be positioned within the FN 202 by passing through the cerebellum 204 from the intrathecal space 222 or through the tissue wall of the 4$^{th}$ ventricle 224.

Figure 6:
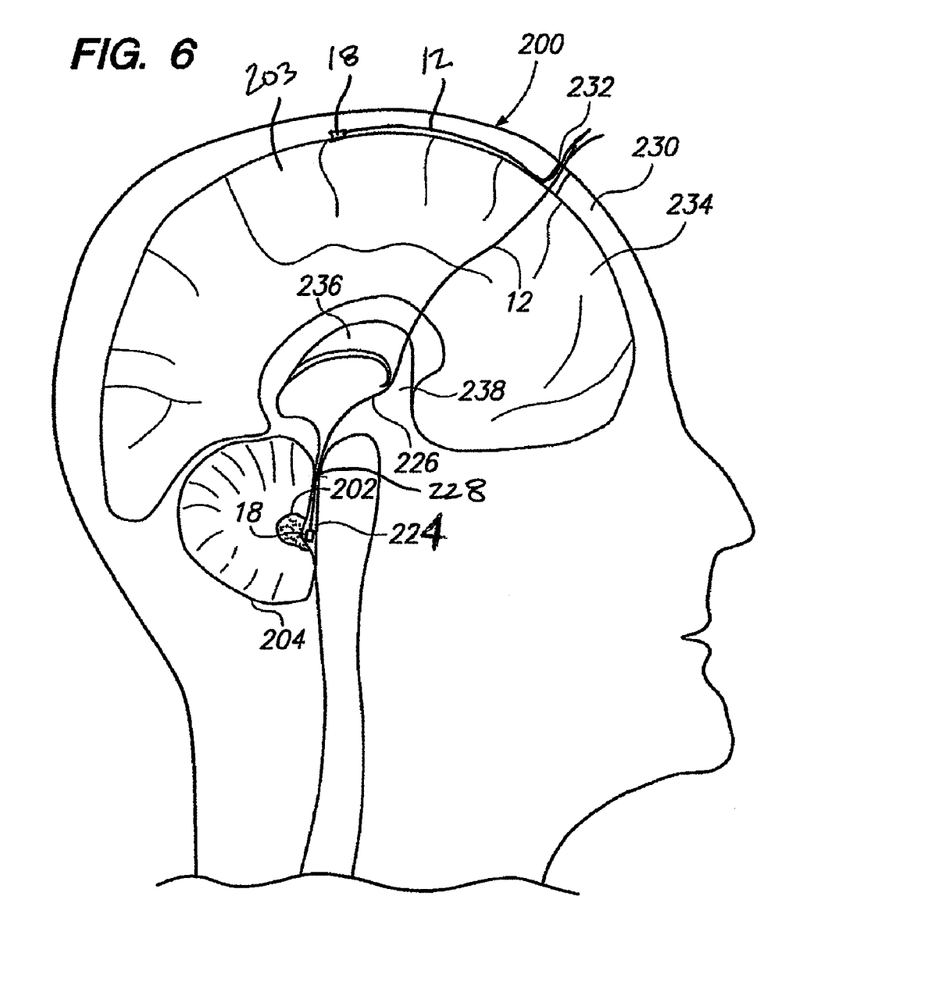
FIG. 6 is a lateral view of one hemisphere of a patient's brain, particularly illustrating routing of the stimulation lead of the system of FIG. 1 to a site adjacent the fastigium nucleus via a cranial burr hole and the ventricular system.

As still another example shown in FIG. 6, the stimulation lead 12 may be delivered into the patient's head 200 directly through the cranium 230, and in this case, a burr hole 232 within the cranium 230. In a manner similar to that used in a ventriculostomy procedure to treat hydrocephalus, the stimulation lead 12, preferably with the aid of an endoscope (not shown) can then be routed through the frontal lobe 234, into the lateral ventricle 236, down through the foramen of Monroe 238 to the 3$^{rd}$ ventricle 226, and down through the Sylvian aqueduct 228 into the 4$^{th}$ ventricle 224 (best shown in FIG. 7). Optionally, a second stimulation lead 12 may be delivered through the burr hole 232, and its electrode 18 placed in contact with the cortical tissue 203.

Although the previous FN delivery and stimulation methods have been described as being used to treat acute stroke patients, they can also be used to treat patients who suffer from any other disease that can be ameliorated by increase blood flow within the brain. For example, patients who suffer from chronic transient ischemic attacks can be treated by increasing the collateral blood flow within the brain. Patients who suffer from cerebral vasospasm as a result of an intracranial bleed to heat trauma can be treated by increasing the blood flow within the brain, which can potentially dilate the spastic vessels. Alzheimer's patients may be treated by increasing the flow of blood within the brain in order to help metabolize amlyoid plaques. Also, although the stimulation techniques described above using electrical stimulation leads, other types of stimulation can be applied to the FN. For example, a drug delivery tube conduit can be placed adjacent the FN for delivering drugs thereto via a pump. Thus, stimulation of the FN can be accomplished using drugs, alone, or in combination with electrical stimulation, It should also be noted that other brain structures, such as the spheno palatine ganglion (SPG) and possibly other hindbrain structures, such as the cerebrum, Rostral Ventral Lateral Medulla, pons, medulla oblongata, the wall of the sylvian aqueduct, the wall of the 4th ventricle, and other brain stem structures, can also be stimulated via electrical stimulation leads and/or drugs in order to increase the amount of blood flow to the brain. These brain structures can be intravascularly accessed via an appropriate intravascular body within the circulatory or ventricular system.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of performing a medical procedure on a patient, comprising:
    introducing a medical device within the patient's head;
    locating the medical device within a cavity of the ventricular system of the patient;
    introducing the medical device from the cavity of the ventricular system into the 4th ventricle of the patient's head; and
    placing the medical device adjacent the fastigium nucleus of the patient's brain.

2. The method of claim 1, wherein the medical procedure is a treatment of a disorder of the patient.

3. The method of claim 2, wherein the disorder is a neurological disorder.

4. The method of claim 3, wherein the neurological disorder is a disorder that can be alleviated by increasing blood flow within the patient's brain.

5. The method of claim 3, wherein the neurological disorder is an acute stroke.

6. The method of claim 3, wherein the neurological disorder is selected from a group consisting of acute stroke, chronic transient ischemic attack, cerebral vasospasm, and Alzheimer's Disease.

7. The method of claim 1, wherein the medical device is placed into direct contact with the fastigium nucleus.

8. The method of claim 1, wherein the medical device is introduced into the patient's head by advancing the medical device within the intrathecal space along the spinal column of the patient.

9. The method of claim 8, wherein the medical device is located within the 4$^{th}$ ventricle by advancing the stimulation lead from the intrathecal space into the 4$^{th}$ ventricle via the foramen of Magendie.

10. The method of claim 8, wherein the medical device is located within the 4$^{th}$ ventricle by advancing the medical device from the intrathecal space into the 4$^{th}$ ventricle via one of the foramina of Luschka.

11. The method of claim 1, wherein the medical device is introduced into the patient's head via a burr hole.

12. The method of claim 1, wherein the medical device is located within the $4^{th}$ ventricle by introducing the medical device into the $3^{rd}$ ventricle of the patient's head and advancing the medical device from the $3^{rd}$ ventricle into the $4^{th}$ ventricle via the Sylvian aqueduct.

13. The method of claim 12, wherein the medical device is introduced into the $3^{rd}$ ventricle by advancing the medical device from a burr hole through the frontal lobe of the patient's brain into the lateral ventricle of the patient's head, and from the lateral ventricle into the $3^{rd}$ ventricle via the foramen of Monroe.

14. The method of claim 1, wherein the medical device is one of an electrical stimulation lead and a drug delivery tube conduit.

15. The method of claim 2, further comprising stimulating the fastigium nucleus with the medical device to treat the neurological disorder.

16. The method of claim 15, wherein the stimulation of the fastigium nucleus increases the flow of blood within the patient's brain.

17. The method of claim 15, further comprising:
introducing another medical device within the head of the patient;
placing the other medical device adjacent cortical tissue of the patient's brain; and
stimulating the cortical tissue with the other medical device to rehabilitate the patient.

\* \* \* \* \*